(12) United States Patent
Bae et al.

(10) Patent No.: US 11,449,210 B2
(45) Date of Patent: Sep. 20, 2022

(54) METHOD FOR PROVIDING AN IMAGE BASE ON A RECONSTRUCTED IMAGE GROUP AND AN APPARATUS USING THE SAME

(71) Applicant: VUNO, INC., Seoul (KR)

(72) Inventors: Woong Bae, Seoul (KR); Seung Ho Lee, Gyeonggi-do (KR)

(73) Assignee: VUNO, INC., Seoul (KR)

(*) Notice: Subject to any disclaimer, the term of this patent is extended or adjusted under 35 U.S.C. 154(b) by 29 days.

(21) Appl. No.: 16/991,713

(22) Filed: Aug. 12, 2020

(65) Prior Publication Data

US 2021/0048941 A1    Feb. 18, 2021

(30) Foreign Application Priority Data

Aug. 13, 2019  (KR) .......................... 10-2019-0098920

(51) Int. Cl.
*G06F 3/048*   (2013.01)
*G06F 3/04845* (2022.01)
(Continued)

(52) U.S. Cl.
CPC ........ *G06F 3/04845* (2013.01); *G06F 3/0489* (2013.01); *G06T 3/4053* (2013.01); *G06F 3/023* (2013.01); *G06F 3/03543* (2013.01)

(58) Field of Classification Search
CPC .... G06F 3/04845; G06F 3/0489; G06F 3/023; G06F 3/03543; G06F 3/0227;
(Continued)

(56) References Cited

U.S. PATENT DOCUMENTS

2007/0183564 A1* 8/2007 Li .......................... A61B 6/465
378/22
2007/0206008 A1* 9/2007 Kaufman ................ G06T 15/06
345/427
(Continued)

FOREIGN PATENT DOCUMENTS

JP    2002-301065 A    10/2002
JP    2004-089507 A    3/2004
(Continued)

OTHER PUBLICATIONS

Dong C et al., Image Super-Resolution Using Deep Convolutional Networks, 2015, V3, IEEE.
(Continued)

*Primary Examiner* — Carolyn R Edwards
(74) *Attorney, Agent, or Firm* — IP & T Group LLP

(57) ABSTRACT

An image providing method performed by a computing apparatus includes acquiring a first image group including at least a portion of a series of images generated for continuous volumes with a first slice thickness belonging to a subject, providing, as a current viewing image, one image of the first image group or one image of a second image group including images generated for continuous volumes with a second slice thickness belonging to the subject, and in response to a first specific input of an input device, repeatedly updating an image provided as the current viewing image with an individual image provided for a subsequent viewing based on a directivity given for the first specific input and, in response to a second specific input of the input device, switching the current viewing image between an image of the first image group and an image of the second image group.

16 Claims, 5 Drawing Sheets

(51) Int. Cl.
*G06F 3/0489* (2022.01)
*G06T 3/40* (2006.01)
*G06F 3/023* (2006.01)
*G06F 3/0354* (2013.01)

(58) Field of Classification Search
CPC ............. G06F 3/038; G06F 2203/0381; G06T 3/4053; G06T 11/008; A61B 5/0073; A61B 5/055; A61B 5/0033; A61B 6/032; A61B 6/4085; A61B 6/5235; G16H 30/20; G16H 30/40
See application file for complete search history.

(56) References Cited

U.S. PATENT DOCUMENTS

| | | | | |
|---|---|---|---|---|
| 2013/0121548 | A1* | 5/2013 | Kovalan | G06T 7/11 382/128 |
| 2013/0195331 | A1* | 8/2013 | Yi | G06V 10/20 382/128 |
| 2019/0290227 | A1* | 9/2019 | Krauss | A61B 6/4035 |
| 2020/0397334 | A1* | 12/2020 | Fang | G06T 15/00 |

FOREIGN PATENT DOCUMENTS

| | | |
|---|---|---|
| JP | 2005-131287 A | 5/2005 |
| JP | 2016-514533 A | 5/2016 |
| JP | 2016-120022 A | 7/2016 |
| JP | 2017-196300 A | 11/2017 |
| JP | 6491471 B2 | 3/2019 |
| KR | 10-2008-0019186 | 3/2008 |
| KR | 10-0893286 | 4/2009 |
| KR | 10-1874348 | 7/2018 |
| KR | 10-1894278 | 9/2018 |
| KR | 10-1898580 | 9/2018 |
| WO | 2015/198835 | 12/2015 |
| WO | 2019/143177 A1 | 7/2019 |

OTHER PUBLICATIONS

Office Action issued by the Japanese Patent Office dated Jun. 29, 2021.

* cited by examiner

[FIG. 1]
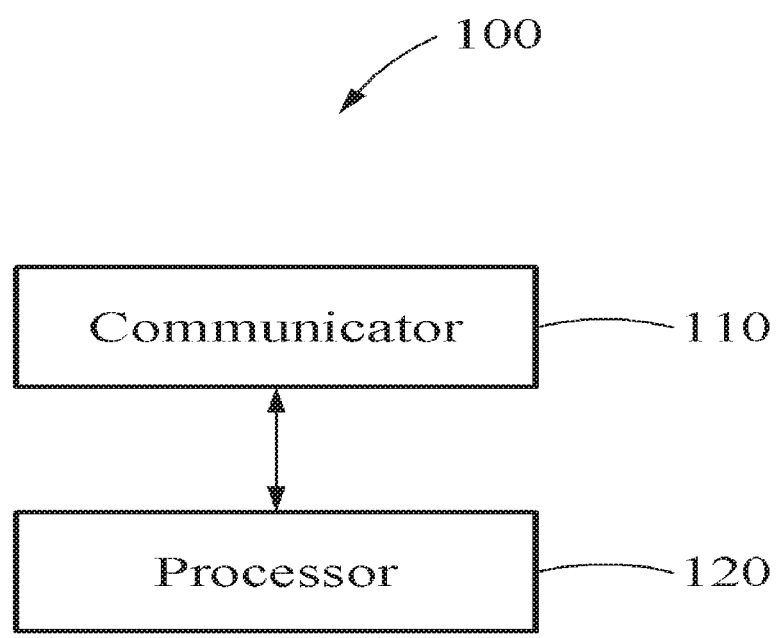

[FIG. 2]
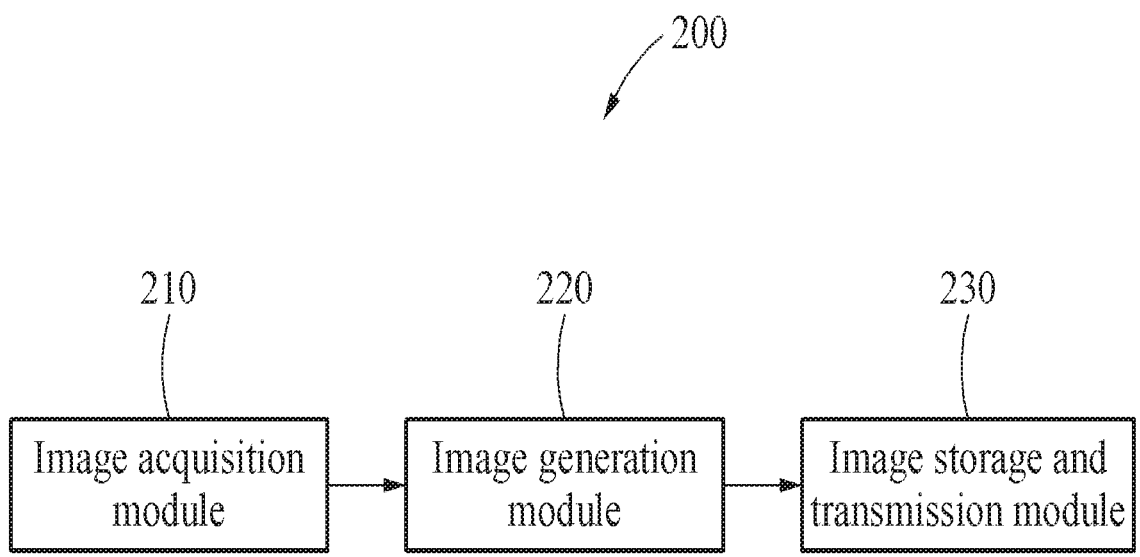

[FIG. 3]
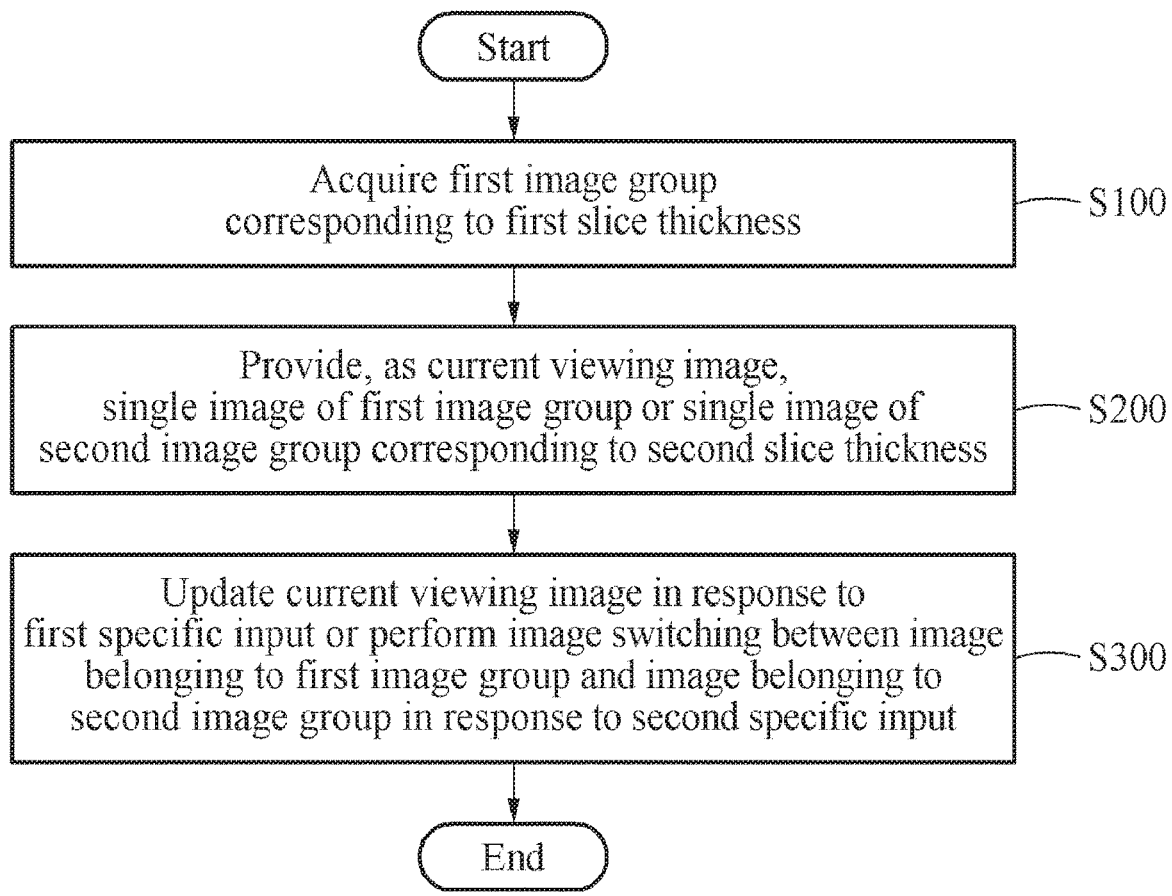

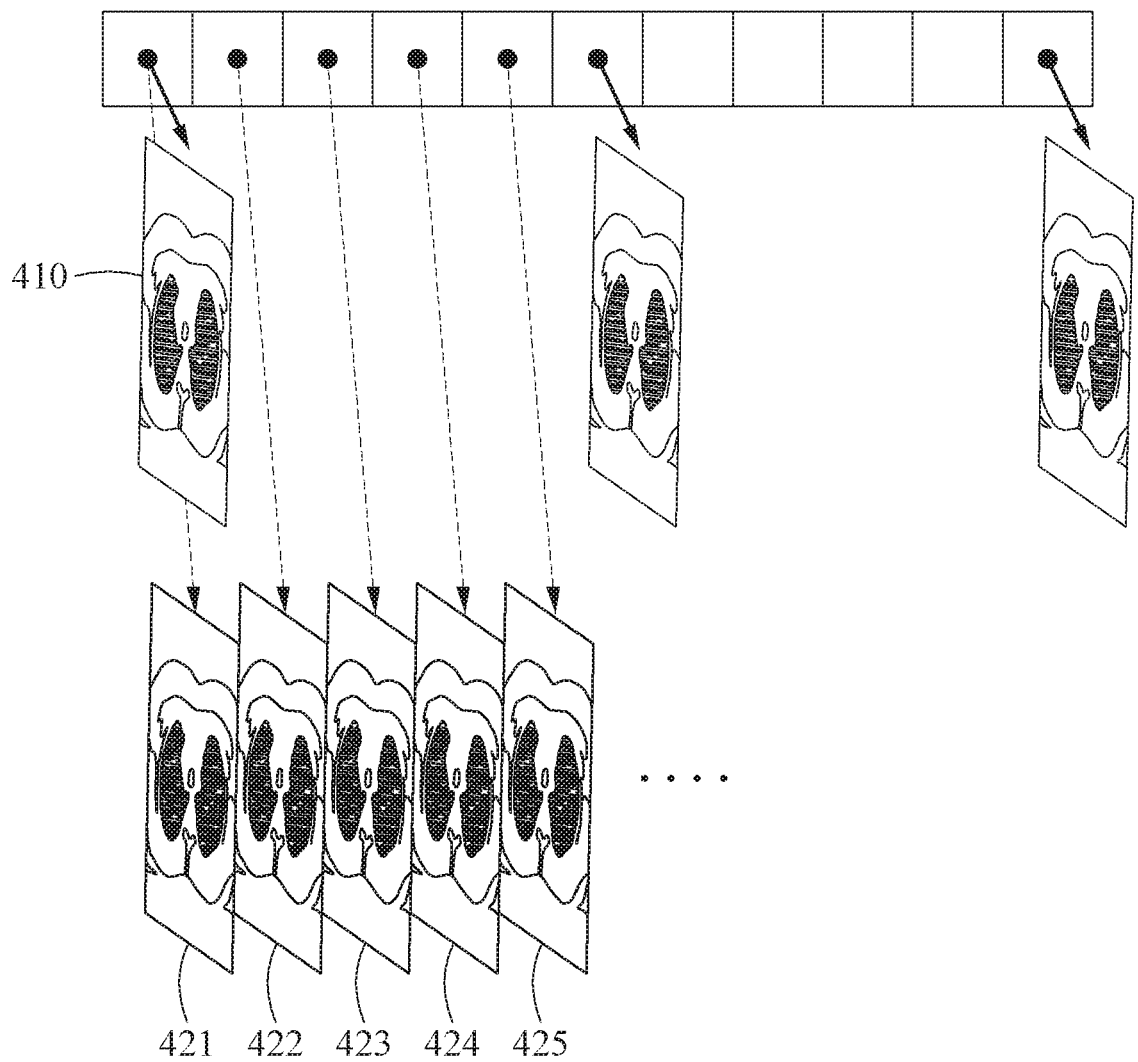
[FIG. 4]

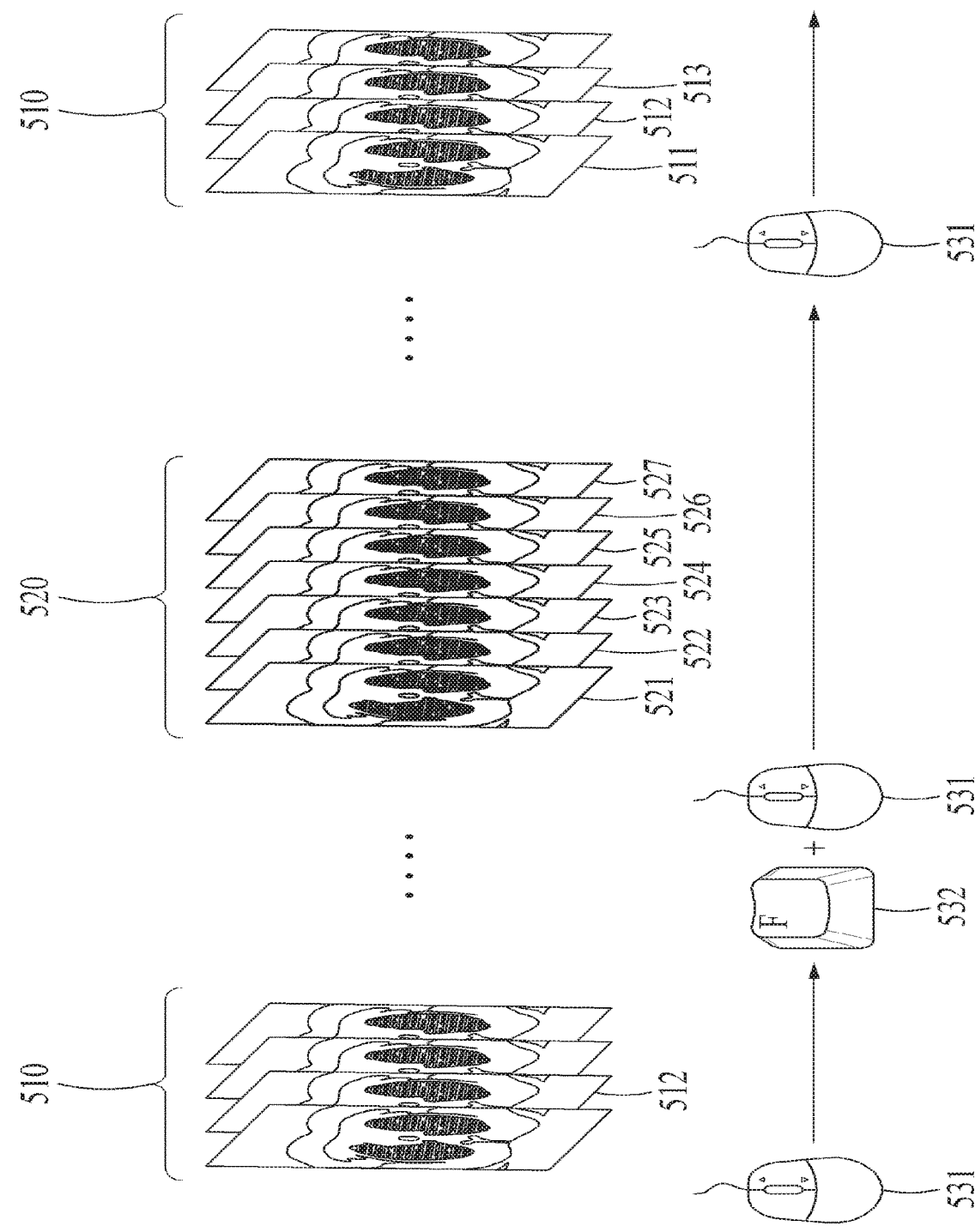
[FIG. 5]

METHOD FOR PROVIDING AN IMAGE BASE ON A RECONSTRUCTED IMAGE GROUP AND AN APPARATUS USING THE SAME

This application claims priority from and the benefit of Korean Patent Application No. 10-2019-0098920 filed on Aug. 13, 2019, which is hereby incorporated by reference in its entirety.

BACKGROUND

1. Field

The present disclosure of the following description relates to an image providing method and an apparatus for performing the image providing method.

2. Related Art

Currently, computed tomography (CT) technology is widely used as an imaging test to analyze lesions and use the same for diagnosis. Individual images constituting a CT image are acquired by projecting a volume with a predetermined slice thickness onto a plane. Here, a thickness of the individual images is referred to as a slice thickness of the CT image for convenience. For example, a 5 mm slice thick image refers to an image acquired by combining information of a 5 mm slice thick space into a single image and thus, the image is blurry, that is, has a low quality.

The thickness of the CT image is differently reconstructed based on the purpose and environment of CT reading. As the thickness becomes thinner, the quality of the image and the accuracy of reading may improve. On the contrary, a number of CT images increases and a relatively long period of time is used for reading accordingly. Also, a relatively large storage space is required to store an image with a thin slice thickness.

In general, in the case of a chest CT image, a 5 mm slice thick image is stored in a database to save a storage space and achieve efficiency of subsequent reading. Here, a small nodule of less than 5 mm based on the 5 mm slice thick image is highly likely to be damaged based on an imaging characteristic. Therefore, to conduct a precise inspection, there is a need for an effective interface capable of alternately verifying a CT image with a 5 mm slice thickness and a relatively thin CT image.

Reference material may include Non-Patent Document 1: Chao Dong et al. (*Image Super-Resolution Using Deep convolutional Networks*, arXiv preprint arXiv: 1501.00092v3, 2015)

SUMMARY

At least one example embodiment provides an interface capable of effectively switching between an image corresponding to a relatively thick slice thickness and an image corresponding to a relatively thin slice thickness and allowing the switched image to be viewed.

At least one example embodiment provides a method that may generate an image of an image group corresponding to a relatively thin slice thickness from an image of an image group corresponding to a relatively thick slice thickness and may readily switch between an image of a thick slice thickness and an image of a thin slice thickness, to assist a doctor to derive a more accurate diagnostic result and to improve an analysis accuracy by a reading assistance system.

Characteristic constitutions of the disclosure to accomplish the aforementioned objectives and to achieve characteristic effects of the disclosure are as follows:

According to an aspect of at least one example embodiment, there is provided an image providing method performed by a computing apparatus, the image providing method including, by the computing apparatus, (a) acquiring a first image group including at least a portion of a series of images generated for continuous volumes with a first slice thickness belonging to a subject or supporting another apparatus interacting with the computing apparatus to acquire the first image group: (b) providing or supporting the other apparatus to provide, as a current viewing image, a single image of the first image group or a single image of a second image group including a series of images generated for continuous volumes with a second slice thickness belonging to the subject; (c) performing a process (c1) of, in response to a first specific input of an input device, repeatedly updating or supporting the other apparatus to update an image provided as the current viewing image with an individual image determined to be provided for a subsequent viewing based on a directivity given for the first specific input and a process (c2) of, in response to a second specific input of the input device, switching or supporting the other apparatus to switch the current viewing image to one of between an image belonging to the first image group and an image belonging to the second image group.

The second slice thickness may be less than the first slice thickness.

The first image group may be generated by projecting, onto a plane, at least a portion of the series of images generated for the continuous volumes with the first slice thickness belonging to the subject, and the second image group may be generated from the first image group based on a super-resolution (SR) scheme.

According to another aspect of at least one example embodiment, there is provided a non-transitory computer-readable record medium storing instructions that, when executed by a processor, cause the processor to perform the image providing method.

According to still another aspect of at least one example embodiment, there is provided a computing apparatus for providing an image generated based on subject information of different slice thicknesses, the computing apparatus including a communicator configured to receive a user input; and a processor configured to perform a process of acquiring a first image group including at least a portion of a series of images generated for continuous volumes with a first slice thickness belonging to a subject or supporting another apparatus interacting with the computing apparatus to acquire the first image group, a process of providing or supporting the other apparatus to provide, as a current viewing image, a single image of the first image group or a single image of a second image group including a series of images generated for continuous volumes with a second slice thickness belonging to the subject, a process of, in response to a first specific input of an input device, repeatedly updating or supporting the other apparatus to update an image provided as the current viewing image with an individual image determined to be provided for a subsequent viewing based on a directivity given for the first specific input and a process of, in response to a second specific input of the input device, switching or supporting the other apparatus to switch the current viewing image between an image belonging to the first image group and an image belonging to the second image group.

According to some example embodiments, through an interface of increasing a reading speed using an image corresponding to a relatively thick slice thickness with respect to an area for which an image corresponding to a relatively thin slice thickness is not required and performing reading using a reconstructed image with a relatively thin slice thickness with respect to an area for which a further precise determination is required, based on a judgement of a reader, it is possible to improve the accuracy of reading and to save a reading time.

For example, according to some example embodiments, it is possible to innovate a workflow in a medical field by saving a time used for the medical staff to perform a diagnosis and by improving a speed and quality of reading.

According to some example embodiments, since it is possible to use medical images used in hospitals in the related art, such as, for example, three-dimensionally acquired ultrasound images, magnetic resonance imaging (MRI) images, etc., a method proposed herein is not dependent on a particular type of an image or platform.

Further areas of applicability will become apparent from the description provided herein. The description and specific examples in this summary are intended for purposes of illustration only and are not intended to limit the scope of the present disclosure.

BRIEF DESCRIPTION OF THE FIGURES

Example embodiments will be described in more in detail with reference to the following figures that are simply a portion of the example embodiments and those having ordinary skill in the art (hereinafter, those skilled in the art) to which this disclosure pertains may readily acquire other figures based on the figures without an inventive work being made:

FIG. 1 is a diagram illustrating an example of a configuration of a computing apparatus configured to perform an image providing method according to an example embodiment;

FIG. 2 is a diagram illustrating an example of hardware or software components of a computing apparatus configured to perform an image providing method according to an example embodiment;

FIG. 3 is a flowchart illustrating an example of an image providing method according to an example embodiment;

FIG. 4 illustrates an example of describing a method of generating and storing an image of a second image group according to an example embodiment; and FIG. 5 illustrates an example of applying an image providing method by a computing apparatus according to an example embodiment.

DETAILED DESCRIPTION

The following detailed description of this disclosure is described with reference to the accompanying drawings in which specific example embodiments of the disclosure are illustrated as examples, to fully describe purposes, technical solutions, and advantages of the disclosure. The example embodiments are described in detail enough for those skilled in the art to carry out the disclosure.

The terms "image" and "image data" used throughout the detailed description and the claims herein refer to multi-dimensional data that includes discrete image factors (e.g., a pixel in a two-dimensional (2D) image and a voxel in a three-dimensional (3D) image). For example, the term "image" may refer to a medical image of a subject collected by cone-beam computed tomography (CBCT), magnetic resonance imaging (MRI), an ultrasound system, or known other medical imaging systems in the related art. Also, the image may be provided in a non-medical context, for example, a remote sensing system, an electron microscopy, and the like.

The term "image" used throughout the detailed description and the claims may refer to an image visible with an eye (e.g., displayed on a video screen) or a digital representation of an image (e.g., a file corresponding to a pixel output of a CT, an MRI detector, and the like).

For clarity of description, although CBCT image data is illustrated in the drawings as image modality, image forms used in various example embodiments include X-ray images, MRI, CT, positron emission tomography (PET), PET-CT, single photo emission computed tomography (SPECT), SPECT-CT, MR-PET, 3D ultra sound images, etc. However, it will be apparent to those skilled in the art that any 3D image and a slide image derived therefrom may be available, without being limited thereto.

The term "Digital Imaging and Communications in Medicine (DICOM)" standard used throughout the detailed description and the claims is a generic term for a plurality of standards used for digital image representation and communication in medical devices. The DICOM standard is published by the American College of Radiology (ACR) and the National Electrical Manufacturers Association (NEMA).

Also, the term "Picture Archiving and Communication System (PACS)" used throughout the detailed description and the claims is a term for systems that perform storage, processing, and transmission according to the DICOM standard. A medical image acquired using digital medical imaging equipment such as X-ray, CT, and MRI may be stored in a DICOM format and may be transmitted to a terminal inside or outside a hospital over a network. Here, a reading result and a medical record may be added to the medical image.

Further, the term "training" or "learning" used throughout the detailed description and the claims refers to performing a machine learning through computing according to a procedure and it will be apparent to those skilled in the art that the term is not intended to refer to a mental action such as an educational activity of a human.

Also, the terms "comprises/includes" used throughout the detailed description and the claims and modifications thereof are not intended to exclude other technical features, additions, components, or operations. Also, "single" or "one" is used to indicate at least one and "another" is limited to at least second or more.

Those skilled in the art may clearly understand a portion of other purposes, advantages, and features of the disclosure from this specification and another portion thereof from implementations of the disclosure. The following examples and drawings are provided as examples only and not to limit the disclosure. Therefore, the detailed description disclosed herein should not be interpreted as a limiting meaning with respect to a specific structure or function and should be interpreted as representative basic data that provides guidelines such that those skilled in the art may variously implement the disclosure as substantially suitable detailed structures.

Further, the disclosure may include any possible combinations of example embodiments described herein. It should be understood that, although various example embodiments differ from each other, they do not need to be exclusive. For example, a specific shape, structure, and feature described herein may be implemented as another example embodiment without departing from the spirit and scope of the disclosure. Also, it should be understood that a location or an arrangement of an individual component of each disclosed example embodiment may be modified without departing from the spirit and scope of the disclosure. Accordingly, the following detailed description is not to be construed as being limiting and the scope of the disclosure, if properly described, is limited by the claims, their equivalents, and all variations within the scope of the claims. In the drawings, like reference numerals refer to like elements throughout.

Unless the context clearly indicates otherwise, the singular forms "a," "an," and "the," are intended to include the plural forms as well. Also, when description related to a known configuration or function is deemed to render the present disclosure ambiguous, the corresponding description is omitted.

Hereinafter, example embodiments of the disclosure are described in detail with reference to the accompanying drawings such that those skilled in the art may easily perform the example embodiments.

FIG. 1 is a diagram illustrating an example of a configuration of a computing apparatus configured to perform an image providing method according to an example embodiment.

Referring to FIG. 1, a computing apparatus 100 according to an example embodiment includes a communicator 110 and a processor 120, and may directly or indirectly communicate with an external computing apparatus (not shown) through the communicator 110.

In detail, the computing apparatus 100 may achieve a desired system performance using a combination of typical computer hardware (e.g., an apparatus including a computer processor, a memory, a storage, an input device and an output device, components of other existing computing apparatuses, etc.; an electronic communication apparatus such as a router, a switch, etc.; an electronic information storage system such as a network-attached storage (NAS) and a storage area network (SAN)) and computer software (i.e., instructions that enable a computing apparatus to function in a specific manner).

The communicator 110 of the computing apparatus 100 may transmit and receive a request and a response with another interacting computing apparatus. As an example, the request and the response may be implemented using the same transmission control protocol (TCP) session. However, it is provided as an example only. For example, the request and the response may be transmitted and received as, for example, a user datagram protocol (UDP) datagram. In addition, in a broad sense, the communicator 110 may include a keyboard, a mouse, and other external input devices to receive a command or an instruction, etc., and a printer, a display, and other external output devices.

Also, the processor 120 of the computing apparatus 100 may include a hardware configuration, such as a micro processing unit (MPU), a central processing unit (CPU), a graphics processing unit (GPU), a tensor processing unit (TPU), a cache memory, a data bus, and the like. Also, the processor 120 may further include a software configuration of an application that performs a specific objective, an operating system (OS), and the like.

FIG. 2 is a diagram illustrating an example of hardware or software components of a computing apparatus configured to perform an image providing method according to an example embodiment.

Those skilled in the art may understand that individual modules of FIG. 2 may be configured through, for example, the communicator 110 or the processor 120 included in the computing apparatus 100, or through interaction between the communicator 110 and the processor 120.

Describing a method and a configuration of an apparatus according to an example embodiment with reference to FIG. 2, the computing apparatus 100 may include an image acquisition module 210 as a component. The image acquisition module 210 may acquire an image included in a first image group that is prestored in a database or acquired from a dedicated device for image capturing. The image included in the first image group may refer to an image that is generated by projecting, onto a plane, continuous volumes with a first slice thickness belonging to a subject. The image of the first image group may be an axial image of the subject. Also, although it is described that images of the first image group and the second image group are generated based on a chest CT image for clarity of description, it may be understood that they may apply to all of general 3D medical images. An image belonging to the first image group may be an image that is generated based on volume information of a relatively thick first slice thickness to save a storage space and to increase a reading speed.

The acquired image of the first image group may be forwarded to an image generation module 220. The image generation module 220 may generate at least one image of the second image group based on the forwarded image. The image of the second image group may refer to an image corresponding to a second slice thickness less than the first slice thickness.

The image generation module 220 may include an artificial neural network trained based on a large number of images of the first image group and images of the second image group corresponding thereto. The image generation module 220 is configured to regenerate an image of the second image group that meets a feature extracted from an image of the first image group. For example, the image generation module 220 may use a full convolutional neural network that is a deep neural network configured to generate an image of the second image group from an image of the first image group. Also, the image generation module 220 may be trained to receive the first slice thickness and the second slice thickness as a parameter and to generate the received image of the first image group as the image of the second image group corresponding to the second slice thickness. The image generation module 220 may be pre-trained by using, as training data, a plurality of training image pairs each including a first training image of the first slice thickness and a second training image of the second slice thickness.

Meanwhile, it is known that a super-resolution (SR) scheme of converting a low resolution image to a high resolution image, that is, increasing a resolution is available. Such SR scheme is described in, for example, Non-Patent Document 1: [Chao Dong et al. *Image Super-Resoution Using Deep Convolutional Networks*, arXiv preprint arXiv: 1501.00092v3, 2015] Since the SR scheme described in this document also extracts a feature of an input image and regenerates an output image suitable for the feature, those skilled in the art may understand that an image of the second image group may be generated by applying the SR scheme.

An image storage and transmission module 230 may store the generated image of the second image group. The image storage and transmission module 230 may store the image of the second image group in the database to match the image of the first image group that is used to generate the image of the second image group. Also, the image storage and transmission module 230 may sort the generated images of the second image group based on a mutual positional relationship between the images of the second image group and may store the images of the second image group based on a sorting result. For example, the image storage module 230 may sort the images of the second image group in order of physical locations of the images of the second image group, that is, depth values corresponding to the images and may store the sorted images in the database.

The image storage and transmission module 230 may provide the external entity with the image of the first image group or the image of the second image group stored in the database. Here, in the case of providing the external entity, the image storage and transmission module 230 may provide the external entity with the image of the first image group or the image of the second image group through a predetermined display device or through a communicator provided therein. The image storage and transmission module 230 may selectively provide the external entity with the image of the first image group or the image of the second image group in response to a request from the reader.

Here, the external entity may include a user of the computing apparatus 100, a manager, a medical expert in charge of the subject, and the like. In addition, it may be understood that any entity that needs the image of the second image group produced from the image of the first image group may be included as the external entity. For example, the external entity may be an external artificial intelligence (AI) device that includes separate AI hardware module and/or software module using the image of the second image group. Also, "external" in the external entity is not construed to exclude an example embodiment in which AI hardware module and/or software module using at least one of the image of the first image group and the image of the second image group are integrated into the computing apparatus 100 and is used to represent that a result of hardware module and/or software module performing the method of the present disclosure, for example, the image of the second image group, is available as input data of another method. That is, the external entity may be the computing apparatus 100 itself.

Meanwhile, the generated image of the second image group may be used for a doctor to easily perform reading and diagnosis.

Based on such images of the first image group and the images of the second image group that are matched and thereby stored, the image storage and transmission module 230 may provide a method that allows a reader to effectively read an image. In the case of a conventional method of individually generating, from a subject, all of an image corresponding to a relatively thick slice thickness and an image corresponding to a relatively thin slice thickness and storing the generated images and alternately verifying independent two images depending on a necessity of the reader to improve the accuracy of reading, the reader needs to alternately verify the independent two images in person, which may cause disconnection of reading. In contrast, herein, an image of the first image group and an image of the second image group are matched to each other and images of the second image group are sorted based on a mutual positional relationship. Therefore, it is possible to provide a method capable of quickly and accurately performing reading without disconnection during an image reading process.

Although FIG. 2 illustrates that the components are implemented in a single computing apparatus for clarity of description, a plurality of computing apparatus 100 configured to perform the method disclosed herein may be configured to interact with each other.

Hereinafter, an image providing method according to an example embodiment is further described with reference to FIGS. 3 to 5.

FIG. 3 is a flowchart illustrating an example of an image providing method according to an example embodiment.

Referring to FIG. 3, in operation S100, a computing apparatus may acquire a first image group including at least a portion of a series of images generated for continuous volumes with a first slice thickness belonging to a subject or may support another apparatus interacting with the computing apparatus to acquire the first image group. According to an example embodiment, the first image group may be generated by project, onto a plane, at least a portion of the series of images generated for the continuous volumes of the first slice thickness belonging to the subject.

In operation S200, the computing apparatus may provide or support the other apparatus to provide, as a current viewing image, a single image of the first image group or a single image of a second image group including a series of images generated for continuous volumes with a second slice thickness belonging to the subject. According to an example embodiment, the second slice thickness may be less than the first slice thickness. The second image group may be generated from the first image group based on an SR scheme.

In operation S300, in response to a first specific input of an input device, the computing apparatus may perform a process of repeatedly updating or supporting the other apparatus to update an image provided as the current viewing image with an individual image determined to be provided for a subsequent viewing based on a directivity given for the first specific input. Here, the first specific input refers to an input for updating the current viewing image and may be a directional input, that is, an input having a directivity. For example, the first specific input may be an input through a mouse scroll having a directivity or an input using a navigation key of a keyboard. In response to an input of the mouse scroll in an upward direction, the computing apparatus may update the current viewing image with an image corresponding to a location directly above in an axial direction of the current viewing image. On the contrary, in response to an input of the mouse screen in a downward direction, the computing apparatus may update the current viewing image with an image corresponding to a location directly below in the axial direction of the current viewing image. The first specific input is not limited to the proposed example and may include any method capable of providing a directional input.

In operation S300, in response to a second specific input of the input device, the computing apparatus may switch or support the other apparatus to switch the current viewing image between an image belonging to the first image group and an image belonging to the second image group. For example, if the current viewing image is an image of the first image group and the second specific input is performed, the computing apparatus may switch the current viewing image to an image included in the second image group corresponding to the current viewing image. As described above, since images of the second image group are matched to an image of the first image group, image switching may be immediately performed, which may lead to preventing disconnection of reading.

According to an example embodiment, the second specific input may be performed based on a toggle key method. For example, if the second specific input is received based on a toggle key in a situation in which an image of the first image group is provided as the current viewing image, the computing apparatus may provide, as the current viewing image, an image belonging to the second image group corresponding to the current viewing image provided at a point in time at which the second specific input is received. Subsequently, if the second specific input is received again based on the toggle key, the computing apparatus may provide, as the current viewing image, an image of the first image group corresponding to the current viewing image provided at a point in time at which the second specific input is received again.

According to another example embodiment, while a predetermined user input corresponding to the second specific input is being maintained, the computing apparatus may provide, as the current viewing image, an image included in the second image group. In detail, if the second specific input is initiated and maintained for 3 seconds in a situation in which an image included in the first image group is provided as the current viewing image, the computing apparatus may provide, as a current image, an image of the second image group corresponding to a current viewing image provided at a point in time at which the second specific input is received and may provide, as the current image, the image of the second image group for 3 seconds for which the second specific input is maintained. If the first specific input is performed in a situation in which the second specific input is maintained, the computing apparatus may perform an operation of updating the current viewing image using the image of the second image group. That is, if the first specific input corresponding to the upward direction is received in a situation in which the second specific input is maintained, the computing apparatus may update the current viewing image with an image of the second image group corresponding to a location directly above in the axial direction of the current viewing image.

Hereinafter, an example of providing an image through the computing apparatus is further described with reference to FIG. 4.

FIG. 4 illustrates an example of describing a method of generating and storing an image of a second image group according to an example embodiment.

Referring to FIG. 4, as described above, the computing apparatus may generate images 421, 422, 423, 424, and 425 corresponding to a second image group from a prestored image 410 of a first image group. For example, the image 410 may be an image included in the first image group corresponding to a 5 mm slice thickness. Each of the images 421, 422, 423, 424, and 425 may be an image included in the second image group corresponding to a 1 mm slice thickness. The five images 421, 422, 423, 424, and 425 may be generated based on the image 410 corresponding to the 5 mm slice thickness. The computing apparatus may mutually match the image 410 and the images 421, 422, 423, 424, and 425 and may store the same in a database. For example, the images 421, 422, 423, 424, and 425 generated based on the image 410 may be matched to the image 410 and thereby stored, and the images 421, 422, 423, 424, and 425 may be sorted and stored based on physical location information, for example, in order of corresponding depth information. Here, the image 410 and the images 421, 422, 423, 424, and 425 may be matched through matching between image identification numbers. For example, if an identification number of the image 410 is A1 and identification numbers of the images 421, 422, 423, 424, and 425 are B1, B2, B3, B4, and B5, A1 and B1 to B5 may be matched and stored in the database. In this manner, all of images included in the second image group may be matched to an image of the first image group corresponding thereto and thereby stored in the database. Also, the images included in the second image group may be sorted based on information about a positional relationship between the images and thereby sorted in the database.

FIG. 5 illustrates an example of applying an image providing method by a computing apparatus according to an example embodiment.

Referring to FIG. 5, each of images 510 and 520 may be an image provided for a reader through an output device. A first specific input 531 refers to an input for the reader to update a current viewing image 512 and may include an input that provides a directivity, such as a mouse scroll, a navigation button of a keyboard, and the like.

In response to receiving the first specific input 531 in a situation in which the image 512 of a first image group corresponding to a 5 mm slice thickness is provided as an initial image for the reader, the computing apparatus may update an image 521. In detail, the reader may view an image 513 corresponding to 5 mm above in a depth axis compared to the current viewing image 512 in response to an input of a mouse scroll in an upward direction, or may read an image 511 corresponding to 5 mm below in the depth axis compared to the current viewing image 512 in response to an input of the mouse scroll in a downward direction.

For further precise reading, if an image 520 of a relatively thinner slice thickness compared to the current viewing image 510 corresponding to the 5 mm slice thickness needs to be viewed, the reader may perform image switching through a second specific input 532. For example, in response to receiving the second specific input 532 from the reader while viewing the current viewing image 512, the computing apparatus may provide one of images 521, 522, 523, 524, and 525 that are matched to the current viewing image 512 and thereby pre-stored. In FIG. 5, each of the images 521, 522, 523, 524, and 525 may be an image with a 1 mm slice thickness generated based on the image 512, and each of images 526 and 527 may be an image of a 1 mm slice thickness generated based on the image 513.

According to an example embodiment, the computing apparatus may provide the switched image 520 while the second specific input 532 is being maintained and may provide the image 510 again if the second specific input 532 is terminated. In a situation in which the second specific input 532 is maintained, the reader may perform updating among the images 521, 522, 523, 524, 525, and 526 through the first specific input 531. This image updating method may be identical to the method described above for the image 510.

If the second specific input 532 is terminated, image switching may be performed to the image 510 corresponding to a current viewing image, for example, the image 525, at a point in time at which the second specific input 532 is terminated.

According to another example embodiment, the second specific input 532 may be performed based on a toggle key method. For example, if the reader performs the second specific input 532, the reader may continuously view the switched image 520 until the second specific input 532 is received again, without a need to maintain the corresponding input.

One of ordinary skill in the art may easily understand that the methods and/or processes and operations described herein may be implemented using hardware components, software components, or a combination thereof based on the example embodiments. For example, the hardware components may include a general-purpose computer and/or exclusive computing apparatus or a specific computing apparatus or a special feature or component of the specific computing apparatus. The processes may be implemented using at least one microprocessor having an internal and/or external memory, a microcontroller, an embedded microcontroller, a programmable digital signal processor or other programmable devices. In addition, or, as an alternative, the processes may be implemented using an application specific integrated circuit (ASIC), a programmable gate array, a programmable array logic (PAL), or other devices configured to process electronic signals, or combinations thereof. Targets of technical solutions of the disclosure or portions contributing to the arts may be configured in a form of program instructions performed by various computer components and stored in non-transitory computer-readable recording media. The media may include, alone or in combination with the program instructions, data files, data structures, and the like. The program instructions recorded in the media may be specially designed and configured for the example embodiments, or may be known to those skilled in the art of computer software. Examples of the media may include magnetic media such as hard disks, floppy disks, and magnetic tapes; optical media such as CD-ROM discs, DVDs, and Blu-ray; magneto-optical media such as floptical disks; and hardware devices that are specially configured to store and perform program instructions, such as ROM, RAM, flash memory, and the like. Examples of program instructions may include a machine code, such as produced by a compiler and higher language code that may be executed by a computer using an interpreter. Examples of program instructions include both machine code, such as produced by a compiler and files containing structural programming languages such as C++ object-oriented programming language and high or low programming languages (assembly languages, hardware technical languages, database programming languages and techniques) to run not only on one of the aforementioned devices but also a processor, a processor architecture, or a heterogeneous combination of combinations of different hardware and software components, or a machine capable of executing program instructions. Accordingly, they may include a machine language code, a byte code, and a high language code executable using an interpreter and the like.

Therefore, according to an aspect of at least one example embodiment, the aforementioned methods and combinations thereof may be implemented by one or more computing apparatuses as an executable code that performs the respective operations. According to another aspect, the methods may be implemented by systems that perform the operations and may be distributed over a plurality of devices in various manners or all of the functions may be integrated into a single exclusive, stand-alone device, or different hardware. According to another aspect, devices that perform operations associated with the aforementioned processes may include the aforementioned hardware and/or software. Such all of the sequences and combinations associated with the processes are to be included in the scope of the present disclosure.

For example, the described hardware devices may be configured to act as one or more software modules in order to perform the operations of the above-described example embodiments, or vice versa. The hardware devices may include a processor, such as, for example, an MPU, a CPU, a GPU, and a TPU, configured to be combined with a memory such as ROM/RAM configured to store program instructions and to execute the instructions stored in the memory, and may include a communicator capable of transmitting and receiving a signal with an external device. In addition, the hardware devices may include a keyboard, a mouse, and an external input device for receiving instructions created by developers.

While this disclosure is described with reference to specific matters such as components, some example embodiments, and drawings, they are merely provided to help general understanding of the disclosure and this disclosure is not limited to the example embodiments. It will be apparent to those skilled in the art that various changes and modifications in forms and details may be made from the example embodiments.

Therefore, the scope of this disclosure is not defined by the example embodiments, but by the claims and their equivalents, and all variations within the scope of the claims and their equivalents are to be construed as being included in the disclosure.

Such equally or equivalently modified example embodiments may include, for example, logically equivalent methods capable of achieving the same results as those acquired by implementing the method according to the example embodiments. Accordingly, the present disclosure and the scope thereof are not limited to the aforementioned example embodiments and should be understood as a widest meaning allowable by law.

What is claimed is:

1. An image providing method performed by a computing apparatus, the image providing method comprising:
    acquiring, by the computing apparatus, first images with a first slice thickness belonging to a subject;
    acquiring, by the computing apparatus, second images with a second slice thickness, thinner than the first slice thickness, belonging to the subject, wherein the second images include a plurality of second image sets, and each second image set includes a plurality of images generated from a corresponding first image based on a neural network and stored in a database so that a matching relationship is made between the first and second images, based on:
    (i) each second image set is matched to a respective one of the first images, with reference to a $1^{st}$ image of the each second image set, and
    (ii) a plurality of images in each second image set is arranged based on a mutual positional relationship;
    providing, by the computing apparatus, one of the first and second images;
    performing, by the computing apparatus, a first process of, in response to a first input updating an image provided as a current viewing image with an image determined to be provided for a subsequent viewing based on a directivity given for the first input and a second process of, in response to a second input, switching the current viewing image between a first image and a corresponding second image based on the matching relationship between the first and second images.

2. The image providing method of claim 1, wherein the second process is performed in response to the second input based on a toggle key scheme.

3. The image providing method of claim 1, wherein the second process is performed while a predetermined user input corresponding to the second input is maintained.

4. A non-transitory computer-readable record medium storing instructions that, when executed by a processor of a computing apparatus, cause the processor to perform the image providing method of claim 1.

5. The image providing method of claim 1, wherein each second image set is matched to the corresponding first image, based on identification numbers of the first and second images.

6. The image providing method of claim 1, wherein the neural network includes a neural network pre-trained by using, as training data, a plurality of training image pairs each including a first training image of the first slice thickness and a second training image of the second slice thickness.

7. A computing apparatus for providing an image, the computing apparatus comprising:
a communicator configured to receive a user input; and
a processor configured to perform a process of acquiring first images with a first slice thickness belonging to a subject, a process of acquiring second images with a second slice thickness, thinner than the first slice thickness, belonging to the subject, wherein the second images include a plurality of second image sets, and each second image set includes a plurality of images generated from a corresponding first image based on a neural network and stored in a database so that a matching relationship is made between the first and second images, based on: (i) each second image set is matched to a respective one of the first images, with reference to a $1^{st}$ image of the each second image set, and (ii) a plurality of images in each second image set is arranged based on a mutual positional relationship, and
a processor configured to perform a process of providing one of the first and second images, a process of, in response to a first input, updating an image provided as a current viewing image with an image determined to be provided for a subsequent viewing based on a directivity given for the first input, and a process of, in response to a second input, switching the current viewing image between a first image and a corresponding second image based on the matching relationship between the first and second images.

8. An image providing method performed by a computing apparatus, the image providing method comprising:
providing, by the computing apparatus, first images corresponding to a first slice thickness belonging to a subject, in order of a corresponding location based on a directivity of a first user input; and
in response to receiving a second user input, providing, by the computing apparatus, second images corresponding to a second slice thickness belonging to the subject, in order of a corresponding location based on the directivity, starting from a second image corresponding to a location of a first image, which is provided at a point in time at which a second user input is received, based on a matching relationship between the first and second images,
wherein the second slice thickness is thinner than the first slice thickness, and
wherein the second images include a plurality of second image sets, and each second image set includes a plurality of images generated from a corresponding first image based on a neural network and the matching relationship between the first and second images is provided by storing the generated images in a database, based on:
(i) each second image set is matched to a respective one of the first images, and
(ii) a plurality of images in each second image set is arranged based on a mutual positional relationship.

9. The image providing method of claim 8, further comprising:
in response to a change in the directivity during a process of providing the second images in ascending order of corresponding locations, providing the second images in descending order of the corresponding locations, and
in response to a change in the directivity during a process of providing the second images in descending order of corresponding locations, providing the second images in ascending order of the corresponding locations.

10. The image providing method of claim 8, wherein the providing of the second images comprises sequentially providing the second images while the second user input is maintained, and, if the second user input is terminated, sequentially providing the first images based on the directivity, starting a first image of the first images corresponding to a second image provided at a point in time at which the second user input is terminated.

11. The image providing method of claim 8, wherein the providing of the second images in order of the corresponding location based on the directivity comprises, if the second user input is additionally received, sequentially providing the first images based on the directivity, starting from a first image corresponding to a second image provided at a point in time at which the second user input is additionally received.

12. A non-transitory computer-readable record medium storing instructions that, when executed by a processor, cause the processor to perform the image providing method of claim 8.

13. The image providing method of claim 8, wherein each second image set is matched to the respective one of the first images, with reference to $1^{st}$ image of the each second image set.

14. The image providing method of claim 8, wherein the second image provided as a starting image in response to receiving the second user input is $1^{st}$ image of a second image set corresponding to the location of first image, which is provided at a point in time at which the second user input is received.

15. The image providing method of claim 8, wherein the plural second images are matched to the corresponding first image, based on identification numbers of the plural second images and the corresponding first image.

16. The image providing method of claim 8, wherein the neural network includes a neural network pre-trained by using, as training data, a plurality of training image pairs each including a first training image of the first slice thickness and a second training image of the second slice thickness.

* * * * *